US010238854B2

(12) United States Patent
Cai

(10) Patent No.: US 10,238,854 B2
(45) Date of Patent: Mar. 26, 2019

(54) METHODS FOR FORMING A TUBE ASSEMBLY UTILIZING A JOINING AGENT

(71) Applicant: TEKNOR APEX COMPANY, Pawtucket, RI (US)

(72) Inventor: Kevin Cai, Cumberland, RI (US)

(73) Assignee: TEKNOR APEX COMPANY, Pawtucket, RI (US)

( * ) Notice: Subject to any disclaimer, the term of this patent is extended or adjusted under 35 U.S.C. 154(b) by 615 days.

(21) Appl. No.: 14/645,885

(22) Filed: Mar. 12, 2015

(65) Prior Publication Data
US 2016/0265698 A1 Sep. 15, 2016

(51) Int. Cl.
A61M 39/10 (2006.01)
A61M 39/08 (2006.01)
A61M 39/12 (2006.01)

(52) U.S. Cl.
CPC ............ A61M 39/10 (2013.01); A61M 39/08 (2013.01); A61M 39/12 (2013.01)

(58) Field of Classification Search
CPC ....... A61M 39/10; A61M 39/08; A61M 39/12
USPC ........................................................ 156/294
See application file for complete search history.

(56) References Cited

U.S. PATENT DOCUMENTS 2,971,876 A   2/1961 Phair
3,919,160 A * 11/1975 Lakshmanan .......... C09J 109/00
                                              524/365
4,588,402 A * 5/1986 Igari .................... A61M 39/10
                                              285/905
4,876,126 A   10/1989 Takemura et al.
5,070,597 A   12/1991 Holt et al.
7,621,884 B2  11/2009 Goehl et al.
8,287,517 B2  10/2012 Hanlon et al.
8,592,018 B2  11/2013 Uehara et al.
8,735,491 B2   5/2014 Kim et al.
8,735,497 B2 * 5/2014 Cavalieri .............. C08F 210/06
                                              525/191
8,871,317 B2  10/2014 Cai et al.
8,871,864 B2  10/2014 Cai et al.
2004/0073192 A1* 4/2004 Flament-Garcia .... A61L 29/049
                                              604/523
2007/0015871 A1  1/2007 Nakamura et al.
2012/0064274 A1  3/2012 Cai et al.
2012/0150150 A1* 6/2012 Cai .................... A61M 25/0014
                                              604/524
2012/0273496 A1 11/2012 Lourido

OTHER PUBLICATIONS

International Search Report dated Jun. 3, 2016.

* cited by examiner

Primary Examiner — Michael N Orlando
Assistant Examiner — Christian Roldan
(74) Attorney, Agent, or Firm — Hudak, Shunk & Farine Co. LPA

(57) ABSTRACT

A method for joining a flexible tube to a connector having a female fitting that allows relatively facile connection and desirable retention force in a short amount of time. Tube assemblies having a tube bonded to the female fitting of the connector with a joining agent composition including an evaporable liquid hydrocarbon are disclosed.

16 Claims, 1 Drawing Sheet

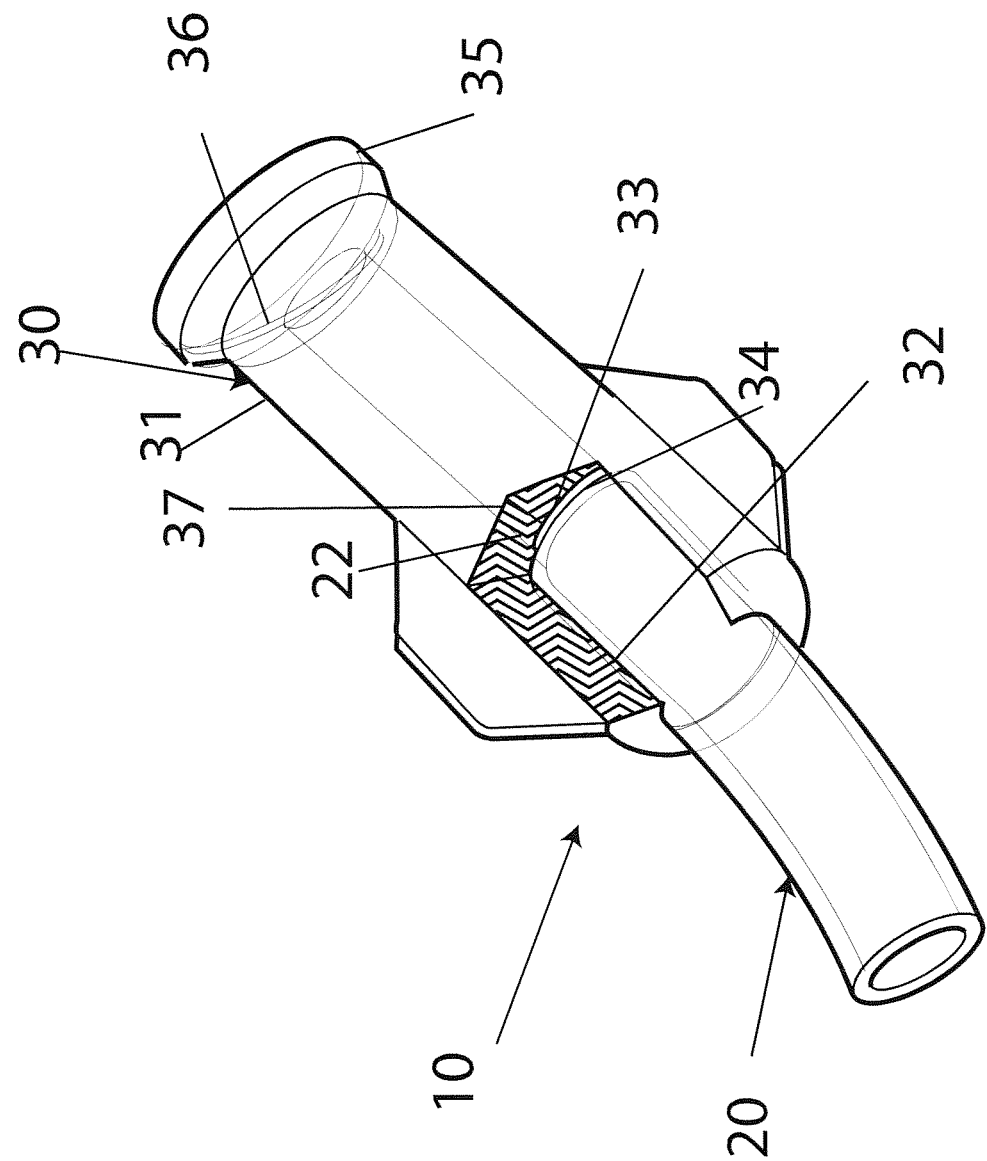

METHODS FOR FORMING A TUBE ASSEMBLY UTILIZING A JOINING AGENT

FIELD OF THE INVENTION

The present invention relates to a method for joining a flexible tube to a connector having a female fitting that allows relatively facile connection and desirable retention force in a short amount of time. Tube assemblies having a tube bonded to the female fitting of the connector with a joining agent composition including an evaporable liquid hydrocarbon are disclosed.

BACKGROUND OF THE INVENTION

In the medical field, medical tubing is utilized to convey fluids to and from a patient. Tubing is also used in various other non-medical fluid transfer fields as known in the art. Tubes are bonded, in some embodiments, to a female fitting wherein the outer diameter of the tube is bonded to the inner diameter of the female fitting.

Flexible tubing made with essentially non-polar surfaces and relatively difficult to bond (co)polymers such as polypropylene, polyethylene, styrenic block copolymers and blends thereof can be difficult to bond to traditional female connectors utilizing a conventional solvent bonding technique, wherein the tubing has an end that is coated, such as by dipping, and then inserted into the female fitting.

To improve bonding between a tube and a connector, different techniques have been developed, see U.S. Pat. Nos. 8,871,864 and 8,871,317, which involve the use of adhesives, U.S. 2012/0150150 which incorporates the use of an insert liner, and U.S. Pat. No. 8,735,491 which utilizes a halogen-free, plasticizer-free thermoplastic elastomer compound reportedly capable of being solvent bonded or welded to another thermal plastic material utilizing cyclohexanone alone or with methyl ethyl ketone.

As evidenced by the various approaches taken, there is a demand for practical and cost effective ways to improve the retention force between tubing and a female fitting of a connector.

SUMMARY OF THE INVENTION

In view of the above, it would be desirable, and is an object of the present invention, to provide a method for joining a flexible tube to a female fitting of a connector with a joining agent composition that a) lubricates one or more of the tube and connector to allow insertion of the tube into the connector, to a desired location, and b) results in high retention force, which can be achieved rapidly, within minutes in some embodiments.

Still another object of the present invention is to provide a method for bonding flexible tubing, preferably thermoplastic elastomeric tubing, having a maximum outer diameter, at least at a surface that contacts the fitting when the tube assembly is formed, that is larger than a maximum inner diameter of the female fitting of a connector with a joining agent composition.

A further object of the present invention is to provide a method for joining a flexible tube to a female fitting of a connector utilizing an evaporable liquid hydrocarbon-containing joining agent composition.

An additional object of the present invention is to provide bonding methods that achieve high retention force, rapidly after joining a tube and a desired connector, provide low assembly costs, and tube assemblies that are relatively easy to produce, which enable mass production.

Yet another object of the present invention is to provide a joining agent composition that includes a hydrocarbon, such as one or more of hexane, heptane, xylenes (one or more of a o-xylene, m-xylene and p-xylene) and toluene. In additional embodiments the joining agent composition further includes a thermoplastic elastomer, preferably a styrenic block copolymer in one embodiment.

In one aspect of the present invention a method for forming a tube assembly is disclosed, comprising the step of obtaining a tube having an outer diameter; obtaining a connector having a female fitting with an inner diameter that is less than the tube outer diameter; applying a liquid joining agent composition comprising a hydrocarbon to one or more of i) the outer diameter of an end portion of the tube and ii) at least a portion of the female fitting inner diameter; joining the tube to the connector to form the tube assembly by inserting the end portion of the tube into the female fitting.

In another aspect of the present invention is a tube assembly is provided, comprising a tube having an end having an outer diameter, the end inserted in, and secured to a female fitting of a connector, wherein prior to insertion the tube outer diameter is greater than an inner diameter of the female fitting, wherein the tube and connector are secured using a joining agent including a hydrocarbon composition.

BRIEF DESCRIPTION OF THE DRAWINGS

The invention will be better understood and other features and advantages will become apparent by reading the detailed description of the invention, taken together with the drawings, wherein:

FIG. 1 is a partial cross-sectional view of one embodiment of a tube assembly according to the present invention, wherein a tube having an end of a greater initial outer diameter has been located within a female fitting of a connector, wherein the inner diameter of the female fitting is smaller than the initial outer diameter of the tube end.

DETAILED DESCRIPTION OF THE INVENTION

In this specification, all numbers disclosed herein designate a set value, individually, in one embodiment, regardless of whether the word "about" or "approximate" or the like is used in connection therewith. In addition, when the term such as "about" or "approximate" is used in conjunction with a value, the numerical range may also vary, for example by 1%, 2%, 5%, or more in various other embodiments.

The invention provides a tube assembly exhibiting desirable retention force between a soft flexible tube and a connector having a female fitting that is achieved rapidly after connection or joining of the tube and connector. The tube and connector are secured using a joining agent composition including a hydrocarbon, wherein the joining agent composition not only serves as a bonding agent, but as a lubricant that facilitates connecting the tube having a larger outer diameter than an inner diameter of the female fitting of the connector.

Referring now to the drawings, FIG. 1 illustrates one embodiment of a tube assembly 10 of the present invention including a flexible tube 20 having a first end 22 joined to a connector 30.

Tube 20 is formed from a relatively soft composition that allows the tube to be flexible. When utilized herein, the terms "tube" and "tubing" are intended to embrace any construction or structure arranged at a substantially radial distance about a longitudinal axis. The intended use of the tube is as a conduit to convey a fluid such as a gas or liquid, or even a flowable solid, such as in a liquid, or a combination thereof.

The tubing can have one or more of the following features: a hollow cylinder having an inner surface and outer surface, independently, with a circular or non-circular cross-section for example oval, elliptical; a longitudinal axis that is linear or non-linear, e.g. bent or curved along all or a portion of the tube length; and one or more of the inner surface and outer surface, such as multi-lumen tubing, having a shape that is variable along the length of the tube. The tube can have one or more, two or more, layers with a single layer being preferred.

Depending upon the application, the tubing can be formed having any desired length, inner diameter, outer diameter and wall thickness. The wall thickness is generally defined as the difference between the outer diameter and inner diameter of the tube at a given cross-sectional area.

The composition of the tube can likewise vary based on the requirements of the end use of the assembly. Examples of compositions that can be utilized include, but are not limited to, various polymers, copolymers, thermoplastic elastomers and thermoplastic vulcanizates. Suitable polymers include, but are not limited to, polyolefins, acrylonitrile-butadiene-styrene resins, silicone homopolymers or block copolymers and polyolefin-styrenic block copolymer-based thermoplastic elastomers.

Thermoplastic elastomer tubing is preferable in various embodiments of the invention and can be utilized to obtain a desirable retention force between the tubing and connector with the use of the joining agent composition. It has been surprisingly found that with difficult to bond flexible tubing, the outer diameter of the tubing needs to be generally from about 1 to about 10%, desirably from about 2 to about 8% and preferably from about 3 to about 5% larger than the inner diameter of female fitting of the connector.

The flexible tubing joined to a connector is relatively soft and flexible as well as easy to bend and manipulate in actual application. In various embodiments the tube hardness ranges generally from about 50 Shore A to about 40 Shore D, desirably from about 65 Shore A to about 92 Shore A and preferably from about 73 Shore A to about 88 Shore A as measured according to ASTM D 2240. In some preferred embodiments, the connector has a greater hardness than the tube.

The wall thickness of tubing can vary, depending on the application. That said, the tube preferably has a wall thickness generally between about 5 to about 40% of the tubing outer diameter, desirably from about 10% to about 35% of the tubing outer diameter, and preferably from about 15% to about 25% of the tubing outer diameter.

The connector 30 can be any suitable construction, and is preferably utilized as a fitting to join tube 20 to another component. Many different styles of connectors are known in the art. In the medical field, one common connector is a Luer lock-type connector, with one embodiment illustrated in FIG. 1. The connector has a body 31 having at one end a female fitting 32 having an inner surface 33 with an inner diameter. The outer diameter of flexible tube 20 is joined to the inner surface 33 of the inner diameter of connector 30 as explained herein. Preferably the female fitting is provided with a seat 34 having an aperture or passageway 37 therein having the diameter less than the diameter of the inner surface 33 and preferably a diameter substantially equal to the inner diameter of tube 20 that allows fluid to pass therebetween. The end 22 of tube 20 preferably contacts the seat 34 upon full insertion into fitting 32. At a second end 35, the connector has a second fitting, opposite the first, female fitting 32 that accepts the tube. The second fitting may optionally have a taper. The second end 35 preferably includes a threaded external surface 36 in one embodiment.

The connector is preferably made from a durable polymeric material, but alternatively can be made from metal or other materials. Suitable polymers include, but are not limited to, polyolefins, polycarbonate (PC) resins, polyurethane, acrylic resins, polyvinyl chloride, acrylonitrile-butadiene-styrene (ABS) resins, PC/ABS alloy, polyesters, olefin-containing alloys, polyacetyls, cyclic olefin copolymer, polyether ether ketone, polyamide, such as nylon, or a fluorocarbon polymer such as polytetrafluoroethylene.

The tube is joined to the connector after applying a joining agent composition comprising a hydrocarbon to one or more of the outer diameter of the end portion of the tube and a portion of the inner diameter of the female fitting. The joining agent includes or consists of one or more hydrocarbons that are liquids at room temperature in various embodiments. The hydrocarbon comprises one or more of hexane, heptane, toluene, o-xylene, m-xylene, and p-xylene.

In one preferred embodiment, the hydrocarbon composition has a boiling point between 50° C. and 200° C., and preferably between about 60° C. and 150° C.

In a further embodiment, the joining agent composition includes one or more of a polymer and thermoplastic elastomer, such as one or more of a polystyrene, styrene butadiene block copolymer, hydrogenated styrene butadiene copolymer, and polyurethane; preferably dissolved or substantially dissolved by the hydrocarbon. The concentration of the one or more of the polymer and thermoplastic elastomer in the hydrocarbon is between 0% or 1% to about 20%, desirably from 0% or 1% to about 15%, and preferably from 0% or 1% to about 10% by weight of the joining agent composition.

In one embodiment, the joining agent composition includes a hydrogenated or saturated styrenic block copolymer comprising at least three blocks with styrene or mono alkenyl arene present in each block, preferably a majority of the monomers of the end blocks and a minority of the monomers in the one or mid-blocks. The styrenic block copolymer has relatively high styrene or mono alkenyl arene content, with the styrene or mono alkenyl arene present in the mid-block(s) arranged randomly or in a controlled distribution.

In various embodiments of the invention, the styrene or mono alkenyl arene is present in a total weight in an amount of greater than 38% and preferably greater than 45% based on the total weight of the random or controlled distribution styrenic block copolymer. In various embodiments, the mid-block of the random or controlled distribution copolymer block has a mono alkenyl arene content of less than 30%, desirably less than 29% by weight.

The controlled distribution block copolymer of the present invention may include the copolymers sold under the trade name Kraton A® Polymers, wherein Kraton A1536 and A1535 are examples.

The joining agent composition can be applied to one or more of a) the outer diameter of an end portion of the tube and b) at least a portion of the female fitting inner diameter. In one embodiment, the end of the tube is dipped in the joining agent composition for a desired period of time, for example from about 0.5 to about 2 seconds, prior to inserting the tube end into the female fitting of the connector. In other embodiments, the joining agent is brushed or sprayed, with a liquid dispenser, onto one or more of the tube and female fitting surfaces to be connected.

In various embodiments of the invention, a tube assembly comprising a tube having an end bonded in a female fitting of a connector has a bond strength of at least 35.6 N (8 Lbf), wherein the tube has an outer diameter from about 1% to about 10% larger than the female fitting inner diameter, wherein the tube has a hardness from about 65 Shore A to about 92 Shore A. In another embodiment of the present invention, a tube assembly comprising a tube having an end bonded in a female fitting of a connector has a bond strength of at least 42.7 N (9.6 Lbf), wherein the tube has a 78 Shore A hardness, wherein a polycarbonate connector is utilized, and wherein the tube has an outer diameter from about 1% to about 10% larger than the female fitting inner diameter, for example, an outer diameter of 4.27 mm and inner diameter of 4.01 to 4.17 mm. Toluene is used as the joining agent in a preferred embodiment.

EXAMPLES

The examples set forth below serve to illustrate methods for joining a flexible tube to a connector having a female fitting and tube assemblies formed utilizing the methods of the invention.

The examples are not intended to limit the scope of the invention.

Tube assemblies consisting of a tube bonded to a connector were prepared by dipping an end portion the tube into solvent (comparative examples) or joining agent, briefly tapping the dipped tube on a paper tissue to remove some or substantially all of the solvent or joining agent inside of the tube, and inserting the tube end into the connector.

With the comparative examples having a small tube outer diameter, the tube could easily be inserted into the connector. To ensure the connector inner surface is sufficiently wetted, the tube was pulled out and immediately reinserted into the connector.

In the comparative examples with a large, oversized tube outer diameter, the tube could not be inserted all the way into the connector. The tube was then pulled out and immediately reinserted into the connector. It was often necessary to re-dip the tubing into solvent before reinserting the tubing into the connector. It was also often necessary to repeat the re-dipping/re-inserting more than 2 times in attempt to fully insert the oversized tube into the connector when using the comparative solvent.

In the case of the invention, the tube was inserted into the connector. To ensure the connector inner surface was properly wetted, the tube was pulled out and immediately reinserted into the connector. No additional dipping/reinserting was needed.

The solvent used in the comparative examples was cyclohexanone. The joining agents used in the examples were pure hydrocarbon, such as heptane, toluene, xylenes; or polymer solution. The polymer solution was prepared by dissolving the polymer into the hydrocarbon solvent. For example, 10 wt. % Kraton A1536 is dissolved in toluene.

The retention force of the assembly between the tubing and connector was measured on an Instron tensile instrument at 20 in/min speed with one inch tube sample length between the Instron clamp and the tubing/connector line. To ensure the tubing/connector assembly was aligned straight to prevent or minimize tilting and false high retention force, an adaptor was used to hold the connector in a straight position. The retention force test was typically done 7 days after the assembly. In a time study shown in Table 3, the retention force was tested after various bonding times. The results of an average retention force of 5-10 bonded samples are reported in the tables. The tubes used in the examples were extruded from grades of various hardness of Medalist® MD-50200 series from Teknor Apex. The connectors were purchased from Qosina. The ABS connector was P/N 65248 with fitting ID of 4.04-4.19 mm. The PC connector was P/N 71636 with fitting ID of 4.01-4.17 mm.

The following test protocols were used for testing:

| Tests | Units | Procedure |
| --- | --- | --- |
| Tubing TPE Hardness (15 sec) | Shore A | ASTM D-2240 |
| Average Retention Force | N (Lbf) | Given Above |

In the tables, a "Yes" entry in the "Easy to Assemble" column means that the tube was inserted into the connector without having to repeat the dipping step prior to attempting to reinsert the tube end into the connector. A "No" entry required at least one additional dipping step and reinsertion, and often could not be inserted fully even with multiple attempts.

TABLE 1

| Experiment Number | Control Solvent or Joining Agent Composition | Easy to Assemble | TPE Hardness 15s delayed Shore A | Tubing OD (mm) | ABS Fitting ID (mm) | Tubing Wall Thickness (mm) | Avg Retention force, N (Lbf) |
| --- | --- | --- | --- | --- | --- | --- | --- |
| Control #1 | Toluene | Yes | 73A | 4.06 | 4.04-4.19 | 0.76 | 26.7 (6.0) |
| Control #2 | Cyclohexanone | No | 73A | 4.27 | 4.04-4.19 | 0.86 | 35.6 (8.0) |
| Example #1 | Toluene | Yes | 73A | 4.27 | 4.04-4.19 | 0.86 | 36.0 (8.1) |
| Example #2 | Heptane | Yes | 73A | 4.27 | 4.04-4.19 | 0.86 | 35.6 (8.0) |
| Example #3 | A1536/Toluene (10%) | Yes | 73A | 4.27 | 4.04-4.19 | 0.86 | 36.9 (8.3) |
| Control #3 | Cyclohexanone | No | 73A | 4.36 | 4.04-4.19 | 0.91 | 38.7 (8.7) |
| Example #4 | Toluene | Yes | 73A | 4.36 | 4.04-4.19 | 0.91 | 38.3 (8.6) |

TABLE 1A

| Experiment Number | Control Solvent or Joining Agent Composition | Easy to Assemble | TPE Hardness 15s delayed Shore A | Tubing OD (mm) | ABS Fitting ID (mm) | Tubing Wall Thickness (mm) | Avg Retention force, N (Lbf) |
|---|---|---|---|---|---|---|---|
| Control #4 | Toluene | Yes | 83A | 4.06 | 4.04-4.19 | 0.76 | 31.6 (7.1) |
| Control #5 | Cyclohexanone | No | 83A | 4.27 | 4.04-4.19 | 0.86 | 50.3 (11.3) |
| Example #5 | Toluene | Yes | 83A | 4.27 | 4.04-4.19 | 0.86 | 49.8 (11.2) |
| Example #6 | Xylene | Yes | 83A | 4.27 | 4.04-4.19 | 0.86 | 49.4 (11.1) |
| Example #7 | Heptane | Yes | 83A | 4.27 | 4.04-4.19 | 0.86 | 52.0 (11.7) |
| Example #8 | A1536/Toluene (10%) | Yes | 83A | 4.27 | 4.04-4.19 | 0.86 | 51.6 (11.6) |
| Control #6 | Cyclohexanone | No | 83A | 4.43 | 4.04-4.19 | 0.84 | 50.3 (11.3) |
| Example #9 | Toluene | Yes | 83A | 4.43 | 4.04-4.19 | 0.84 | 52.5 (11.8) |

In Table 1, Control #1 illustrates that tubing having substantially the same outer diameter as an inner diameter of the fitting is relatively easy to assemble but results in lower average retention force as compared to Control #2 and Examples #1, #2 and #3. Control #2 utilizes tubing having an outer diameter larger than the fitting and cyclohexanone as a solvent. The combination provides acceptable retention force but it is difficult to assemble the tubing into the connector. To fully insert the tubing into the connector, the partially inserted tube had to be pulled out of the connector, dipped into solvent, and reinserted into the connector. Sometimes, it was necessary to repeat the above procedure more than two times, which is not practical for mass production. Examples #1, #2 and #3 utilized tube having a larger outer diameter than the inner diameter of the fitting. The Examples were easy to assemble and provide a desirable retention force due to the use of the specified joining agents.

Control #3 utilized an even larger tube outer diameter, and even greater average force is exhibited as compared to Control #2 but the tube assembly was not easy to assemble. Example #4 illustrates that tubing having even a larger outer diameter than Example #1 exhibited even greater retention force using the toluene joining agent, while maintaining ease of assembly.

In Table 1A, the controls and examples showed the same comparison as in Table 1 for tubing made with a 83 Shore A hardness TPE instead of a 73 Shore A hardness. The retention forces are all higher than those in Table 1 due to the higher hardness of the TPE.

TABLE 2

| Experiment Number | Control Solvent or Joining Agent Composition | Easy to Assemble | TPE Hardness 15s delayed Shore A | Tubing OD (mm) | PC Fitting ID (mm) | Tubing Wall Thickness (mm) | Avg Retention force, N (Lbf) |
|---|---|---|---|---|---|---|---|
| Control #7 | Toluene | Yes | 73A | 4.06 | 4.01-4.17 | 0.76 | 26.7 (6.0) |
| Control #8 | Cyclohexanone | No | 73A | 4.27 | 4.01-4.17 | 0.86 | 38.7 (8.7) |
| Example #10 | Toluene | Yes | 73A | 4.27 | 4.01-4.17 | 0.86 | 40.5 (9.1) |
| Example #11 | Heptane | Yes | 73A | 4.27 | 4.01-4.17 | 0.86 | 36.9 (8.3) |
| Example #12 | Xylene | Yes | 73A | 4.27 | 4.01-4.17 | 0.86 | 37.8 (8.5) |
| Control #9 | Cyclohexanone | No | 73A | 4.36 | 4.01-4.17 | 0.91 | 45.4 (10.2) |
| Example #13 | Toluene | Yes | 73A | 4.36 | 4.01-4.17 | 0.91 | 40.5 (9.1) |

TABLE 2A

| Experiment Number | Control Solvent or Joining Agent Composition | Easy to Assemble | TPE Hardness 15s delayed Shore A | Tubing OD (mm) | PC Fitting ID (mm) | Tubing Wall Thickness (mm) | Avg Retention force, N (Lbf) |
|---|---|---|---|---|---|---|---|
| Control #10 | Toluene | Yes | 83A | 4.06 | 4.01-4.17 | 0.76 | 37.4 (8.4) |
| Control #11 | Cyclohexanone | No | 83A | 4.27 | 4.01-4.17 | 0.86 | 51.2 (11.5) |
| Example #14 | Toluene | Yes | 83A | 4.27 | 4.01-4.17 | 0.86 | 53.4 (12.0) |
| Example #15 | Heptane | Yes | 83A | 4.27 | 4.01-4.17 | 0.86 | 53.4 (12.0) |
| Example #16 | Xylene | Yes | 83A | 4.27 | 4.01-4.17 | 0.86 | 51.6 (11.6) |
| Control #12 | Cyclohexanone | No | 83A | 4.36 | 4.01-4.17 | 0.91 | 54.7 (12.3) |
| Example #17 | Toluene | Yes | 83A | 4.36 | 4.01-4.17 | 0.91 | 54.7 (12.3) |

Table 2 discloses test results of a tube assembly having a thermoplastic elastomer tube and a polycarbonate connector. Control #7 illustrates that tubing having substantially the same outer diameter as an inner diameter of the fitting is relatively easy to assemble but results in lower average retention force as compared to Control #6 and Examples #10, #11 and #12. Control #8 utilizes tubing having an outer diameter larger than the fitting and cyclohexanone as a solvent. The combination provides acceptable retention force, but it is difficult to assemble the tubing into the connector. To fully insert the tubing into the connector, the partially inserted tube had to be pulled out of the connector, dipped into solvent, and reinserted into the connector. Sometimes, it was necessary to repeat the above procedure more than two times, which is not practical for mass production. Examples #10, #11 and #12 utilized tubing having a larger outer diameter than the inner diameter of the fitting and the specified joining agents. The Examples were easy to assemble and provide a desirable retention force.

Control #9 utilized a larger tube outer diameter and achieved greater average force as compared to Control #8, but, again, the tube assembly was not easy to assemble. Example #13 illustrates that tubing having even a larger outer diameter than Example #10 exhibited even greater retention force using toluene as joining agent.

In Table 2A, the controls and examples showed the same comparison as in Table 2 for tubing made with a 83 Shore A hardness TPE instead of a 73 Shore A hardness. The retention forces are all higher than those in Table 1 due to the higher hardness of the TPE.

TABLE 3

| Experiment Number | Bonding Time before Retention Test, Hour(s) | Easy to Assemble | Avg Retention force, N (Lbf) |
|---|---|---|---|
| Example #14 | 0.12 | Yes | 42.7 (9.6) |
| Example #15 | 0.61 | Yes | 43.1 (9.7) |
| Example #16 | 7.11 | Yes | 44.0 (9.9) |
| Example #17 | 21.14 | Yes | 44.0 (9.9) |
| Example #18 | 77.51 | Yes | 45.8 (10.3) |
| Example #19 | 147.46 | Yes | 46.7 (10.5) |
| Example #20 | 244.02 | Yes | 47.6 (10.7) |

Table 3 illustrates the low variation of retention force with solvent bonding time for a tube assembly formed with a tube having 78 Shore A hardness and a PC connector. The tube had an outer diameter of 4.27 mm and wall thickness of 0.86 mm. The PC connector had a female fitting ID of 4.01-4.17 mm. The bonding was done using toluene as the joining agent. Unlike what was disclosed in U.S. Pat. No. 8,735,491, namely high retention force reportedly can be achieved after multiple days of bonding, desirable high retention force was achieved almost instantly with the bonding method disclosed herein.

While in accordance with the patent statutes the best mode and preferred embodiment have been set forth, the scope of the invention is not limited thereto, but rather by the scope of the attached claims.

What is claimed is:

1. A method for forming a tube assembly, comprising the steps of:
   obtaining a flexible tube having an outer diameter;
   obtaining a connector having a body having at one end a female fitting having an inner surface with an inner diameter, wherein the female fitting has a seat having an aperture having a diameter less than the female fitting inner diameter, wherein the flexible tube outer diameter is 1 to 10% larger than the female fitting inner diameter, wherein the connector has a greater hardness than the flexible tube;
   applying a liquid joining agent composition comprising a hydrocarbon that consists of carbon and hydrogen atoms to one or more of i) the outer diameter of an end portion of the flexible tube and ii) at least a portion of the female fitting inner diameter;
   joining the flexible tube to the connector to form the tube assembly by inserting the end portion of the flexible tube into the female fitting.

2. The method according to claim 1, wherein the outer diameter is 2 to 8% larger than the female fitting inner diameter.

3. The method according to claim 1, wherein the outer diameter is 3 to 5% larger than the female fitting inner diameter.

4. The method according to claim 1, wherein the hydrocarbon comprises one or more of hexane, heptane, toluene, o-xylene, m-xylene, and p-xylene.

5. The method according to claim 3, wherein the hydrocarbon composition comprises one or more of heptane, toluene, o-xylene, m-xylene, and p-xylene.

6. A method for forming a tube assembly, comprising the steps of:
   obtaining a flexible tube having an outer diameter;
   obtaining a connector having a body haying at one end a female fitting having an inner surface with an inner diameter, wherein the female fitting has a seat having an aperture having a diameter less than the female fitting inner diameter wherein the flexible tube outer diameter is 1 to 10% larger than the female fitting inner diameter, wherein the connector has a greater hardness than the flexible tube;
   applying a liquid joining agent composition to one or more of i) the outer diameter of an end portion of the flexible tube and ii) at least a portion of the female fitting inner diameter;
   joining the flexible tube to the connector to form the tube assembly by inserting the end portion of the flexible tube into the female fitting;
   wherein the joining agent composition consists of i) a hydrocarbon that consists of carbon and hydrogen atoms and ii) a thermoplastic elastomer, wherein the thermoplastic elastomer comprises one or more of styrenic block copolymer, polystyrene, styrene butadiene block copolymer, and hydrogenated styrene butadiene copolymer.

7. A method for forming a tube assembly, comprising the steps of:
   obtaining a flexible tube having an outer diameter;
   obtaining a connector having a body having at one end a female fitting having an inner surface with an inner diameter, wherein the female fitting has a seat having an aperture having a diameter less than the female fitting inner diameter wherein the flexible tube outer diameter is 1 to 10% larger than the female fitting inner diameter, wherein the connector has a greater hardness than the flexible tube;
   applying a liquid joining agent composition comprising one or more of i) the outer diameter of an end portion of the flexible tube and ii) at least a portion of the female fitting inner diameter;
   joining the flexible tube to the connector to form the tube assembly by inserting the end portion of the flexible tube into the female fitting;

wherein the liquid joining agent composition comprises i) a hydrocarbon that consists of carbon and hydrogen atoms and ii) a styrenic block copolymer having three blocks with styrene or monoalkenyl arene present in each block, wherein the styrene or mono alkenyl arene in the mid-block is present in a random or controlled distribution form.

8. The method according to claim 4, wherein the flexible tube comprises a thermoplastic elastomer composition comprising a styrenic block copolymer and a polyolefin, and wherein the connector comprises one or more of ABS, polycarbonate, and an acrylic resin.

9. The method according to claim 1, wherein the flexible tube has a wall thickness generally between about 5-40% of the tubing outer diameter.

10. The method according to claim 4, wherein the flexible tube has a hardness of about 50 Shore A to about 40 Shore D.

11. The method according to claim 1, wherein the tube assembly has a bond strength of at least 35.6 N (8 Lbf), and wherein the flexible tube has a hardness from about 65 Shore A to 92 Shore A.

12. The method according to claim 4, wherein the hydrocarbon composition has a boiling point between 50° C. and 200° C.

13. The method according to claim 8, wherein the total concentration of the thermoplastic elastomer is from 1 to 20 parts by weight based on 100 total parts by weight of the joining agent composition.

14. The method according to claim 1, wherein the tube assembly has a bond strength of at least 42.7 N (9.6 Lbf) at 0.12 hours after the joining step, wherein the flexible tube has a 78 Shore A hardness, wherein a polycarbonate connector is utilized.

15. The method according to claim 1, wherein the female fitting seat aperture has a diameter substantially equal to an inner diameter of the flexible tube.

16. The method according to claim 15, wherein a second end of the connector has a threaded external surface.

* * * * *